United States Patent [19]

Angstadt et al.

[11] Patent Number: 5,493,067
[45] Date of Patent: * Feb. 20, 1996

[54] SOLID SUPERACID ALKYLATION CATALYST COMPOSITIONS AND ALKYLATION METHOD USING THE SAME

[75] Inventors: Howard P. Angstadt, Media, Pa.; Elmer J. Hollstein, Wilmington, Del.; Chao-Yang Hsu, Media, Pa.

[73] Assignee: Sun Company, Inc. (R&M), Philadelphia, Pa.

[*] Notice: The portion of the term of this patent subsequent to Feb. 13, 2013, has been disclaimed.

[21] Appl. No.: 151,446

[22] Filed: Nov. 12, 1993

[51] Int. Cl.$^6$ .................................................. C07C 2/62
[52] U.S. Cl. ................................. 585/731; 585/730
[58] Field of Search ........................ 585/731, 730

[56] References Cited

U.S. PATENT DOCUMENTS

| | | | |
|---|---|---|---|
| 4,918,041 | 4/1990 | Hollestein et al. | |
| 4,956,519 | 9/1990 | Hollstein et al. | |
| 5,036,035 | 7/1991 | Baba et al. | |
| 5,212,136 | 5/1993 | Angstadt et al. | |
| 5,214,017 | 5/1993 | Angstadt et al. | |
| 5,321,196 | 6/1994 | Ohgoshi et al. | 585/709 |
| 5,321,197 | 6/1994 | Angstadt et al. | 585/721 |
| 5,324,881 | 6/1994 | Kresge et al. | 585/721 |
| 5,391,532 | 2/1995 | Soled et al. | 502/210 |
| 5,420,092 | 5/1995 | Soled et al. | 502/210 |
| 5,422,327 | 6/1995 | Soled et al. | 502/242 |

FOREIGN PATENT DOCUMENTS

| | | |
|---|---|---|
| 61-183230 | 8/1986 | Japan. |
| 61-242641 | 10/1986 | Japan. |
| 1-245853 | 10/1989 | Japan. |
| 1-245854 | 10/1989 | Japan. |

OTHER PUBLICATIONS

Ito et al., "Solid acid catalysts for isobutane alkylation" *CA Selects Abstract No. 106: 216817b, Issue 13, 20, (1987)*.

"Superacids Catalyze Alkylation of Xylene", *Chemical Week, Nov. 25, 1987, p. 28*.

*Primary Examiner*—Asok Pal
*Attorney, Agent, or Firm*—Q. Todd Dickinson; Stephen T. Falk

[57] ABSTRACT

Isoparaffins and olefins are alkylated by contact with a solid superacid such as sulfated zirconia optionally containing added metals, and containing added heteropolyacids (HPA's) or polyoxoanions (POA's). The presence of HPA's or POA's in the solid superacid catalyst results in higher yields of desired high-octane components in the product mixture than are obtained in the absence of HPA's or POA's.

24 Claims, No Drawings

SOLID SUPERACID ALKYLATION CATALYST COMPOSITIONS AND ALKYLATION METHOD USING THE SAME

BACKGROUND OF THE INVENTION

The reaction of isobutane with low ($C_2$–$C_5$) molecular weight olefins to produce $C_6$–$C_9$ paraffins is commonly referred to as alkylation. In commercial practice this reaction is carried out in the presence of acid type catalysts such as concentrated sulfuric acid or HF. The reaction is an important process to the petroleum industry as it upgrades chemical compounds in crude oil for which there may be little value to high octane fuel components. The two acids mentioned above are the catalysts of choice as the process is now practiced commercially, but each of them while producing a satisfactory alkylate for fuel blending has serious drawbacks. The use of HF presents a significant ecological hazard should it escape into the atmosphere, and the sulfuric acid process is very corrosive and energy consuming as it needs to be operated at below ambient temperatures in order to provide a satisfactory alkylate. Certain solid compositions with acidic properties have been found to catalyze this reaction as subsequently disclosed.

THE PRIOR ART

Solid superacid catalysts have been proposed for use as alkylation catalysts. See for example Hollstein et al U.S. Pat. Nos. 4,918,041 and 4,956,519 issued Apr. 17, 1990 and Sep. 11, 1990 respectively, disclosing solid superacid catalysts useful in alkylation and other reactions comprising a sulfated calcined metal oxide or hydroxide of Group III or Group IV, e.g. zirconium; metal oxide or hydroxide of Group V, Group VI or Group VII, e.g. manganese; 3 O and a metal oxide or hydroxide of Group VIII, e.g. iron. See also Angstadt et al U.S. Pat. No. 5,212,136 issued May 18, 1993, disclosing solid superacid catalysts useful as alkylation catalysts comprising sulfated and calcined mixtures of a support comprising an oxide or hydroxide of a Group IV-A element, an oxide or hydroxide of molybdenum and an oxide or hydroxide of a Group I-B, II-B, III-A, III-D, IV-B, V-A or VI-A metal other than molybdenum, or a metal of the Lanthanide Series of the Periodic Table. See also Angstadt et al U.S. Pat. No. 5,214,017 issued May 25, 1993, disclosing solid superacid catalysts useful as alkylation catalysts, comprising sulfated and calcined mixtures of a support comprising an oxide or hydroxide of a Group IV-A element, an oxide or hydroxide of a Group VI, VII or VIII metal, an oxide or hydroxide of a Group I-B, II-B, III-A, III-B, IV-B, V-A or VI-A metal and an oxide or hydroxide of a metal of the Lanthanide Series of the Periodic Table. other disclosures of solid superacids useful in alkylation processes are contained in:

(1) Hatakeyama et al Japanese Kokai Patent, SHO 61-183230, Aug. 15, 1986, disclosing sulfated zirconia alkylation catalysts and their use in alkylation of butenes and isobutane at a temperature in the range from −20° C. to +10° C. under pressure of from 0 to 50 kg/cm$^2$, the alkylation being carried out in either gaseous phase or liquid phase, the latter preventing inactivation that is caused by deposition of coke on the catalyst and extending the life of the catalyst, and the reaction being carried out either by a suspension or fixed bed process.

(2) Abstract No. 106:216817b, CA Selects: Catalysis (Applied & Physical Aspects), Issue 13, Jun. 29, 1987, Ito et al, Jpn. Kokai Tokyo Koho JP 61,242,641 (86,242,641), Oct. 28, 1986, disclosing alkylation catalysts prepared from sulfate ion or its precursors and rare earth metals or their compounds, e.g. lanthanum nitrate, on supports consisting of Group IV-A or IV-B metal hydroxides or oxides, followed by calcination and stabilization, and the use of such catalysts in alkylation of isobutane with isobutene at 60° C.

(3) In the Ito et al Japanese Kokai Patent, SHO 61-242641, Oct. 28, 1986, application SHO 60-84515 filed Apr. 22, 1985, which corresponds to (2) above, a solid acidic catalyst for alkylation of isoparaffin with olefin is disclosed. The catalyst is obtained by adding a rare earth element or its compounds, and a sulfate radical or its precursor to a supporting member made of hydroxide or oxide of Group IV metals, followed by sintering at 400°–800° C., for stabilization. Hydroxide or oxide of at least one type of metal chosen from titanium, zirconium, hafnium, silicon, germanium and tin is used; particularly hydroxide or oxide of zirconium or titanium is preferred. Tantalum and cerium or their compounds are disclosed as the most desirable rare earths; praseodymium, neodymium, samarium and gadolinium are also disclosed. The alkylation reaction is preferably run in liquid phase.

(4) In Hosoi et al Japanese Kokai Patent HEI 1-245853 disclosure date Oct. 2, 1989, Application No. SHO 63-73409, Mar. 29, 1988, solid acid catalyst for alkylation is disclosed, containing a Group IIb, Group Va, Group Va or Group VIIa metal or compound thereof, and sulfate or precursor of sulfate, on a carrier made from hydroxide or oxide of Group III and/or Group IV metals, followed by baking and stabilizing. Sulfated zinc/zirconium hydroxides, chromium/zirconium hydroxides, vanadium/zirconium hydroxides, manganese/zirconium hydroxides, zinc/titanium hydroxides, zirconium/titanium hydroxides, zirconium/aluminum hydroxides are disclosed. It is desirable to run the reaction in liquid phase.

(5) In Shimizu et al Japanese Kokai Patent HEI 1-245854, disclosure date Oct. 2, 1989, Application No. SHO 63-73410, Mar. 29, 1988, a solid acid catalyst for alkylation of isobutane by olefins is obtained by adding a sulfate or precursor thereof to a carrier comprising compound metal hydroxides or compound metal oxides of two or more kinds of metals selected from titanium, zirconium, silicon and tin. Sulfated zirconia/titania, zirconia/tin oxide, zirconium/silicon catalysts are disclosed. Running the reaction in liquid phase is disclosed as desirable.

(6) Chemical Week, Nov. 25, 1987, on page 28, discloses superacids obtained by sulfating zirconium, titanium and iron oxides, as catalysts for alkylation of orthoxylene by styrene.

DESCRIPTION OF THE INVENTION

The present invention provides an alkylation process which minimizes the processing problems of the existing processes using sulfuric acid or HF, and obtains benefits from the use of heteropolyacids (HPA's) or polyoxoanions (POA's) in combination with solid superacids.

The HPA's or POA'S, when incorporated with the strongly acidic solid acids, which are generated for example by treating zirconia with ammonium sulfate and then calcining at high temperatures, produce superior alkylation catalysts. That is, the alkylate produced by the HPA modified sulfated zirconia has a higher proportion of 8-carbon compounds than that obtained when using only the sulfated zirconia, and the proportion of the 8-carbon fraction containing the high octane trimethylpentanes is also greater than that obtained either with the more traditional acids or the unmodified solid superacids. Additionally the amount of heavier ends, $C_9$–$C_{12}$, produced during the alkylation is greatly reduced. Additionally the alkylation reaction can be carried out at room temperature to provide good yields of alkylate product, thus eliminating the need for sub-ambient cooling and resulting in a more energy efficient operation.

PREPARATION OF SUPERACID HPA OR POA CATALYST

The solid superacid catalyst according to the invention is prepared by incorporating an HPA or POA onto a sulfated zirconia or other Group III or Group IV oxide support by suitable techniques such as those which are known to those skilled in the art of catalyst preparation. Techniques for preparing sulfated and calcined solid superacids comprising oxides of Group III or IV elements such as zirconia are disclosed for example in the Hollstein et al and Angstadt et al patents supra, the disclosures of which are hereby incorporated by reference. The incorporation of HPA or POA into the catalyst is typically done by forming an aqueous solution of an ammonium salt of the HPA or POA and impregnating the solid superacid with the solution; typically the impregnation is done by the incipient wetness technique in which the amount of water used to make the solution is about the amount which will be absorbed by the solid superacid upon contact of the latter with the solution. The order of the sulfating and calcining of the catalyst in relation to the impregnation of the Group IV oxides with HPA or POA is not critical; however, it is preferred to impregnate the Group IV oxide with HPA or POA following the sulfation of the Group IV oxide and prior to the final calcining of the composition. The weight of HPA or POA relative to Group III or IV oxide in the composition according to the invention will typically be in the range from about 0.1% to about 10%, preferably 0.5% to 5%, but any suitable ratio may be used. Since the HPA or POA is typically more expensive to manufacture than the Group IV oxide, it is preferred to use the minimum amount of HPA or POA consistent with the desired activity of the composition as a catalyst for improvement of isomer distribution in the alkylation product. Preferred HPA's or POA's for use according to the invention are those having the Keggin structure represented by the formula $H_4XM_{12}O_{40}$, wherein X may be any metal from Groups IV, V, VI, VIII, or the Lanthanide series of the Periodic Table, and M is any element in Groups III, IV, V, or VI, however HPA's or POA's of the Anderson and Dawson types are also anticipated to produce effective alkylation catalysts when placed upon a solid superacid support. Alkylation results are given in Table I showing that the catalyst compositions of the invention provide higher concentrations of 8-carbon containing species and lower amounts of C9–C12 heavy products than does a catalyst prepared from the superacid zirconia support alone and than are produced using the traditional sulfuric or HF acid processes. Additionally, the amount of the high octane trimethylpentanes produced within the 8-carbon fraction is also significantly greater than that obtained from the traditional processes, thus leading to a higher octane alkylate. The support upon which the heteropolyacid is incorporated need not be entirely composed of a single component such as sulfated zirconia. Mixtures of zirconia with other appropriate oxides such as the oxides from elements in Groups III-A and B and IV-A and B of the Periodic Table may be used. Mixtures of these oxides along with zirconia, upon impregnation with the appropriate HPA and sulfating, provide superior solid-acid alkylation catalysts. For example, silica-zirconia, titania-zirconia, alumina-zirconia and hafnia-zirconia represent appropriate supports for sulfation and impregnation within the scope of the invention. In place of zirconia, other Group III-A and B and Group IV-A and B oxides, or mixtures thereof, may be employed.

The HPA or POA which is used in the catalyst according to the invention may be (1) an azide-promoted HPA or POA as disclosed in Lyons et al U.S. Pat. No. 4,803,187 issued Feb. 7, 1989, the formula of which is disclosed as $K_6PW_{11}VO_{40}N_3$, (2) a site-specific framework-substituted HPA or POA as disclosed in Ellis et al U.S. Pat. No. 4,898,989 issued Feb. 6, 1990, wherein three atoms of molybdenum, tungsten, vanadium or combinations thereof have been replaced with three different metal atoms, which may be for example iron, nickel, zinc, chromium or combinations thereof, (3) HPA's having the formula $H_z(X_kM_nO_y)$ where X is a group IIIA-VIA element, M is a transition metal, k is 1–5, n is 5–20, y is 18–62, and z is 1–6 and corresponding POA's as disclosed in Lyons et al U.S. Pat. No. 4,916,101 issued Apr. 10, 1990, (4) site-specific, framework substituted HPA's or POA's wherein three atoms of molybdenum, tungsten or vanadium or combinations thereof have been replaced with three different metal atoms, two of which are selected from the group consisting of iron, chromium, manganese and ruthenium, and the third of which is different from said two and is selected from the group consisting of transition metals, and in addition to (1) to (4) above this paragraph, the prior art HPA and POA referred to in (1) to (4), such as *Heteropoly and Isopoly Oxo-metalates*, Pope et al, Springer-Verlag, New York, 1983. HPA's and POA's generally are suitable for use in the catalysts according to the invention, while the HPA's and POA's disclosed in (1) to (4) above are preferred.

ALKYLATION CATALYZED BY COMPOSITION OF INVENTION

In the method according to the invention, a feedstock comprising isoparaffins and olefins is contacted with a solid superacid catalyst containing sulfated Group III or IV element and HPA or POA under alkylation conditions. The alkylation according to the invention can be carried out either in the presence or in the absence of an added gas such as hydrogen.

The method of the invention can be carried out with the hydrocarbon reactants and products either in gaseous phase or liquid phase. Liquid phase operation provides advantages over gaseous phase operation in that equipment costs and utility costs are lower, and lower catalyst deactivation rates result. Liquid phase operation with a solid superacid catalyst has the advantage over existing alkylation processes using liquid catalysts in that liquid reactants and products do not have to be separated from a liquid catalyst as well as each other. When liquid phase operation is used, the temperature and pressure conditions are so chosen that the reactants and/or products are in liquid phase.

The invention provides in one embodiment an improved process for the production of alkylate which comprises alkylating a paraffin with an olefin at alkylation conditions which include a paraffin to olefin volume ratio of about 1:1 to about 100:1, a temperature of from about −40° C. to about 200° C., a pressure of from about 1 atmosphere to about 200 atmospheres, a liquid hourly space velocity of from about 0.01 to about 30 in the presence of a solid superacid catalyst containing HPA or POA as herein specified, which may or may not be attended by the presence of hydrogen in the feed. Preferred temperatures and pressures are from about −25° C. to about 125° C. and from about 5 to about 50 atmospheres. Reactor effluents pass to a distillation column wherein unreacted reactants are separated from products and recycled through the reactor and products are passed to gasoline-making facilities.

Where HPA's or POA's are referred to herein, it is understood that mixtures of HPA's and POA's may also be employed.

EXAMPLES

The following examples illustrate the invention.

Examples 1–4

A small (300 ml) Parr reactor was charged with 20 gms. of dry catalyst and 50 mls. of isobutane. With stirring a 15/1 feed of isobutane/butene-2 was added at the rate of 43 mls./hr. for four hours. At the end of the addition the reactor was allowed to stir an additional hour. The product was withdrawn and analyzed by gaschromatography to determine the carbon number distribution which is reported in Table I, and a complete isomer distribution through the 8-carbon fraction, which is reported in Table II.

TABLE I

ALKYLATE COMPOSITION

| | | RUN NUMBER | | | |
|---|---|---|---|---|---|
| | H2SO4 | 114 ZrO2/SO4 | 178 H4SiW12O40 | 171 H4SiMo12O40 | 179 H3PMo12O40 |
| C-3 | 0.00 | 0.34 | 1.14 | 1.24 | 1.21 |
| C-5 | 5.17 | 34.79 | 7.37 | 6.00 | 10.19 |
| C-6 | 5.37 | 11.30 | 3.51 | 3.20 | 4.26 |
| C-7 | 5.26 | 9.14 | 6.80 | 6.10 | 7.17 |
| C-8 | 66.38 | 37.66 | 77.19 | 76.74 | 72.69 |
| C-9 | 4.73 | 5.72 | 2.53 | 3.31 | 3.11 |
| C-10 | 1.83 | 0.58 | 0.73 | 1.38 | 0.70 |
| C-12 | 5.24 | 0.47 | 0.69 | 1.98 | 0.63 |
| C→12 | 0.01 | 0.00 | 0.00 | 0.00 | 0.00 |

TABLE II

ALKYLATE ISOMER DISTRIBUTION

| | | RUN NUMBER | | | |
|---|---|---|---|---|---|
| | H2SO4 | 114 SrO2/SO4 | 178 H4SiW12O40 | 171 H4SiMo12O40 | 179 H4PMo12O4 |
| 2-MeC4 | 5.726 | 34.704 | 7.455 | 6.075 | 10.325 |
| OTHER C5 | 0.010 | 0.222 | 0.000 | 0.000 | 0.000 |
| TOTAL C5 | 5.737 | 34.926 | 7.455 | 6.075 | 10.325 |
| 2,2-DMeC4 | 0.001 | 3.715 | 0.170 | 0.078 | 0.369 |
| 2,3-DMeC4 | 5.455 | 2.384 | 1.847 | 1.837 | 2.047 |
| 2-MeC5 | 0.000 | 3.651 | 0.979 | 0.841 | 1.239 |
| 3-MeC5 | 0.548 | 1.497 | 0.553 | 0.494 | 0.650 |
| TOTAL C6 | 6.004 | 11.248 | 3.549 | 3.250 | 4.306 |
| 2,2-DMeC5 | 0.000 | 1.248 | 0.060 | 0.025 | 0.149 |
| 2,4-DMeC5 | 3.162 | 4.020 | 4.689 | 3.917 | 4.745 |
| 2,2,3-TMeC4 | 0.246 | 0.213 | 0.102 | 0.113 | 0.114 |
| 3,3-DMeC5 | 0.000 | 0.915 | 0.153 | 0.078 | 0.272 |
| 3-MeC6 | 0.154 | 0.721 | 0.221 | 0.250 | 0.254 |
| 2,3-DMeC5 | 1.813 | 1.553 | 1.445 | 1.577 | 1.503 |
| 3-EtC5 | 0.148 | 0.508 | 0.187 | 0.217 | 0.220 |
| OTHER C7 | 0.000 | 0.074 | 0.000 | 0.000 | 0.000 |
| TOTAL C7 | 5.523 | 9.251 | 6.868 | 6.187 | 7.267 |
| 2,4-TMeC5 | 27.420 | 17.440 | 38.221 | 37.088 | 37.241 |
| 2,2-DMeC6 | 0.011 | 0.896 | 0.196 | 0.191 | 0.290 |
| 2,5-DMeC6 | 4.405 | 1.488 | 1.158 | 1.742 | 1.186 |
| 2,4-DMeC6 | 2.855 | 1.220 | 0.000 | 2.227 | 0.000 |
| 2,2,3-TMeC5 | 1.139 | 5.767 | 11.225 | 7.392 | 10.483 |
| 3,3-DMeC5 | 0.000 | 0.351 | 0.094 | 0.078 | 0.123 |
| 2,3,4-TMeC5 | 16.073 | 3.771 | 10.289 | 13.120 | 8.946 |
| 2,3,3-TMeC5 | 15.794 | 5.712 | 15.549 | 13.631 | 14.086 |
| 2,3-DMeC6 | 2.943 | 0.582 | 1.013 | 1.646 | 0.914 |
| 3-Et-2-MeC5 | 0.091 | 0.037 | 0.051 | 0.078 | 0.044 |
| 3-MeC7 | 0.057 | 0.148 | 0.034 | 0.078 | 0.044 |
| 3,4-DMeC6 | 0.518 | 0.148 | 0.255 | 0.399 | 0.237 |
| 4-MeC7 | 0.050 | 0.129 | 0.034 | 0.069 | 0.035 |
| 3-Et-3-MeC5 | 0.002 | 0.000 | 0.000 | 0.000 | 0.000 |
| OTHER C8 | 0.020 | 0.037 | 0.000 | 0.025 | 0.000 |
| TOTAL C8 | 71.381 | 37.725 | 78.120 | 77.764 | 73.629 |

TABLE II-continued

ALKYLATE ISOMER DISTRIBUTION

| | H2SO4 | 114 SrO2/SO4 | 178 H4SiW12O40 | 171 H4SiMo12O40 | 179 H4PMo12O4 |
|---|---|---|---|---|---|
| 2,2,5-TMeC8 | 2.574 | 3.604 | 1.413 | 1.603 | 1.837 |
| OTHER C9 | 1.462 | 1.922 | 1.149 | 1.750 | 1.318 |
| TOTAL C9 | 4.036 | 5.527 | 2.562 | 3.354 | 3.155 |
| TOTAL C10 | 1.714 | 0.582 | 0.740 | 1.395 | 0.712 |
| TOTAL C12 | 5.226 | 0.471 | 0.698 | 2.010 | 0.633 |
| TOTAL > C12 | 0.364 | 0.000 | 0.000 | 0.000 | 0.000 |
| SUM (AREA %) | 99.984 | 99.732 | 99.992 | 100.035 | 100.026 |
| CALC RES OCT | 93.50 | 92.33 | 98.70 | 96.55 | 98.12 |

In Table I, the leftmost column indicates the number of carbon atoms in the various portions of the alkylate product. The columns headed 178, 171 and 179 show the percentages of the various components of the alkylate product, grouped according to the number of carbon atoms in the components, obtained in three runs according to the invention in which the catalyst used contained sulfated zirconia and three different heteropolyacids having the formula shown in the column heading. The column headed 114 shows the results of a comparison run using sulfated zirconia alone as the catalyst. The column headed $H_2SO_4$ shows the results of a comparison run using sulfuric acid as the catalyst.

The superiority of the catalysts of the invention, used in Runs 178, 171 and 179, in producing the desired C-8 compounds is shown in Table I.

In Table II, the leftmost column indicates the various isomeric components of the product. The columns headed $H_2SO_4$, 114, 178, 171 and 179 have the same significations as in Table I. The catalyst used in Run 114 was obtained by mixing aqueous zirconyl nitrate and aqueous ammonium hydroxide to obtain a reaction slurry, which is filtered at about pH 7, and the damp filter cake was washed with de-ionized water, pelletized, dried at 150° C., and calcined in an oven at about 500° C. for 4.0 hours. The calcined pellets were added slowly to a beaker containing 1.0 normal sulfuric acid solution. The sulfuric acid solution was decanted after 2 hours. The pellets were calcined again at 500° C. for 4 hours.

The catalyst used in Run 178 was obtained by a procedure similar to that of Run 114, except that an aqueous solution of the ammonium salt of the heteropolyacid $H_4SiW_{12}O_{40}$ was used to impregnate the zirconium oxide pellets prior to the final calcination; the weight of HPA relative to zirconia in the product composition was about 2%. The catalysts used in Runs 171 and 179 were obtained by similar procedure to Run 114, but using the heteropolyacids $H_4SiMo_{12}O_{40}$ and $H_3PMo_{12}O_{40}$, respectively, in place of the HPA used in Run 114.

The superiority of the catalysts according to the invention, used in Runs 178, 171 and 179, to sulfated zirconia as used in Run 114, in producing such desired products as 2,2,4-trimethylpentane, 2,2,3-trimethylpentane, 2,3,4-trimethylpentane and 2,3,3-trimethylpentane, is shown in Table II. Table II also shows that, in addition to the previously noted advantages of the solid catalysts of the invention over sulfuric acid, the catalysts of the invention also produce a greater yield of desired trimethylpentanes than sulfuric acid produces.

The method of the invention is applicable generally to prior art alkylations of alkanes with olefins with acidic catalysts. Preferred paraffins or alkanes for alkylation reactions according to the invention have 2 to 6 carbon atoms per molecule and include ethane, propane, n-butane, isobutane, pentanes, hexanes and mixtures thereof. Preferred olefins or alkenes for such reactions also have 2 to 6 carbon atoms per molecule and include ethylene, propylene, 1-butene, 2-butene, isobutene, pentenes, hexenes and mixtures thereof.

The invention claimed is:

1. Method of alkylating isoparaffins and olefins which comprises contacting a feedstock comprising isoparaffins and olefins with a catalyst comprising a combination of solid superacid and heteropolyacid or polyoxoanion under alkylation conditions.

2. Method according to claim 1 wherein said contacting is at temperature in the range from about –40° C. to about 200° C., and pressure in the range from about 1 atmosphere to about 200 atmospheres.

3. Method according to claim 1 wherein said solid superacid comprises sulfated zirconia, sulfated titania, sulfated iron oxide or halogenated alumina.

4. Method according to claim 3 wherein said solid superacid comprises sulfated zirconia.

5. Method according to claim 4 wherein said solid superacid comprises an oxide or hydroxide of a group VIII metal.

6. Method according to claim 5 wherein said metal is iron.

7. Method according to claim 5 wherein said metal is cobalt.

8. Method according to claim 3 wherein said solid superacid has been sulfated with ammonium sulfate.

9. Method according to claim 1 wherein said solid superacid contains 5 to 15 weight percent of sulfate ion.

10. Method according to claim 1 wherein the contacting is in the absence of added gas.

11. Method according to claim 1 wherein said heteropolyacid or polyoxoanion is $H_4SiW_{12}O_{40}$ or the corresponding polyoxoanion.

12. Method according to claim 1 wherein said heteropolyacid or polyoxoanion is $H_4SiMo_{12}O40$ or the corresponding polyoxoanion.

13. Method according to claim 1 wherein said heteropolyacid or polyoxoanion is $H_4PMo_{12}O_{40}$ or the corresponding polyoxoanion.

14. A new composition of matter, a heteropolyacid or polyoxoanion supported on a solid superacid comprising a sulfated oxide or hydroxide of a Group III or Group IV element.

15. Composition according to claim 14 wherein said solid superacid catalyst comprises sulfated zirconia, sulfated titania, sulfated iron oxide or halogenated alumina.

16. Composition according to claim 15 wherein said solid superacid catalyst comprises sulfated zirconia.

17. Composition according to claim 16 wherein said catalyst comprises an oxide or hydroxide of a Group VIII metal.

18. Composition according to claim 17 wherein said metal is iron.

19. Composition according to claim 17 wherein said metal is cobalt.

20. Composition according to claim 14 wherein said composition has been sulfated with ammonium sulfate.

21. Composition according to claim 14 containing 5 to 15 weight percent of sulfate ion.

22. Composition according to claim 14 wherein said heteropolyacid or polyoxoanion is $H_4Si_{12}WO_{40}$ or the corresponding polyoxoanion.

23. Composition according to claim 15 wherein said heteropolyacid or corresponding polyoxoanion is $H_4SiMoO_{40}$ or the corresponding polyoxoanion.

24. Composition according to claim 14 wherein said heteropolyacid or polyoxoanion is $H_4PMO_{12}O_{40}$ or the corresponding polyoxoanion.

* * * * *